United States Patent [19]

Palmer

[11] 4,020,785
[45] May 3, 1977

[54] PLANT MOISTURE INDICATOR

[76] Inventor: Walter E. Palmer, 266 Connecticut, San Francisco, Calif. 94107

[22] Filed: May 19, 1976

[21] Appl. No.: 688,086

[52] U.S. Cl. .............................. 116/118 A; 73/73
[51] Int. Cl.² .................. G01N 25/56; G01N 33/24
[58] Field of Search ........... 116/118 A; 73/73, 337; 324/12; 47/1 R

[56] References Cited
UNITED STATES PATENTS

| | | | |
|---|---|---|---|
| 1,219,390 | 3/1917 | Grigsby | 73/337 X |
| 1,920,502 | 8/1933 | Goss | 73/337 |
| 3,019,638 | 2/1962 | Klein | 73/73 |
| 3,555,216 | 1/1971 | Fenner | 73/337 X |

OTHER PUBLICATIONS

Publ. *The Divining Rod* by Arthur J. Ellis, 1917, U.S. Geological Survey (Dept. of Interior), pp. 7–10.
Publ. "*New Wood-Element Hygrostat*" by October Issue 1933, Scientific American p. 183.

Primary Examiner—Richard C. Queisser
Assistant Examiner—Daniel M. Yasich
Attorney, Agent, or Firm—Robert G. Slick

[57] ABSTRACT

A plant moisture indicator is provided comprising a piece of wood cut across the grain with a moisture retardant substance applied to one side of the indicator, whereby the indicator will tend to bend in the presence of moisture and straighten up when dry. Preferably the device is constructed in the form of a U having two such opposed members, whereby the U will close in the presence of moisture and open in the absence of moisture.

2 Claims, 6 Drawing Figures

PLANT MOISTURE INDICATOR

SUMMARY OF THE INVENTION

A number of plant moisture indicators have been proposed, none of which has proved to be entirely satisfactory.

Some of the moisture indicators have involved a complex structure which makes them so expensive that it is not practical to employ one for every pot.

Other moisture indicators have appeared which have proved unstable over a period of time so that the indicator rapidly loses its effectiveness.

Still other indicators have been provided which operate on the conductivity of the soil and are thus not true moisture indicators since they will indicate O even when immersed in distilled water. In other words, they tend to measure the concentration of salts in the soil rather than just moisture.

Other indicators are difficult to read and require a careful comparison with a standard.

In accordance with the present invention, a simple moisture indicator is provided which is very inexpensive, both from the standpoint of materials and labor in making the same. Thus, it is entirely practical for the home gardener to employ one in every pot. The indicator has a long shelf and service life.

Further, in accordance with the present invention, an improved moisture indicator is provided which gives a true indication of moisture and not merely the conductivity of the soil A further advantage of the structure of the present invention is that it is easily adaptable for plants requiring moisture at various depths. As is later explained in detail, the device can be inserted in soil to various depths depending on the particular plant needs.

A still further advantage of the device of the present invention is that it can be read even from a distance.

Other objects and features of the invention will be brought out in the balance of the specification.

DESCRIPTION OF THE PREFERRED EMBODIMENTS

Figure 1:
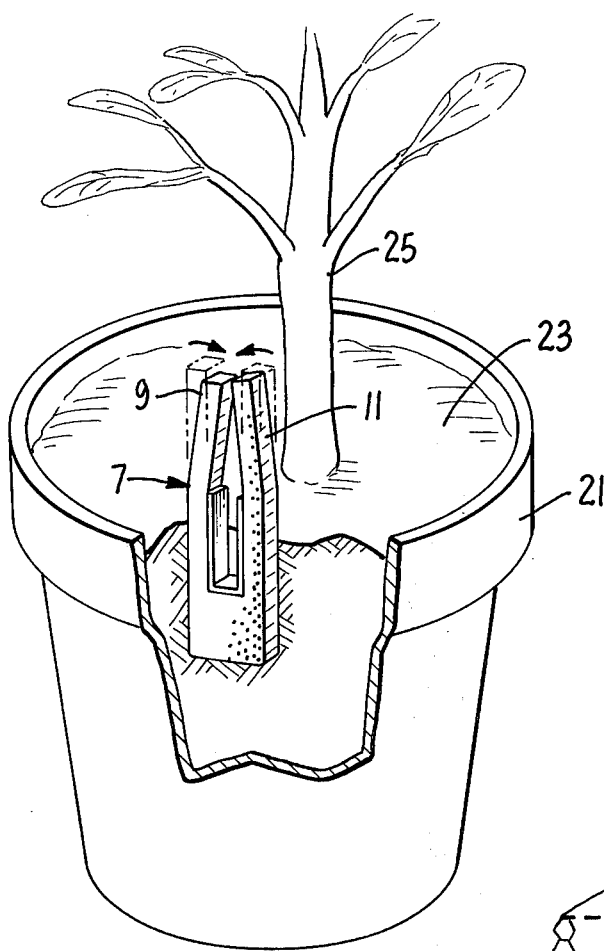
FIG. 1 is a perspective view, partly in section, showing a moisture indicator made in accordance with the present invention in use on a plant.
Figure 2:
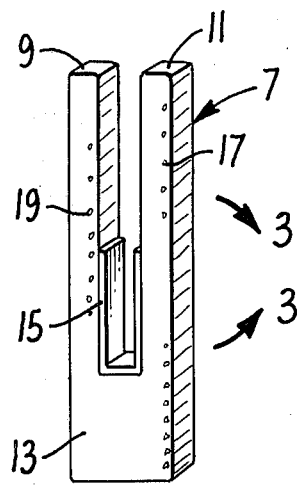
FIG. 2 is a perspective view of the moisture indicator.

The moisture indicator of the present invention is generally designated 7 and consists of a U-shaped member made of wood, having arms 9 and 11 joined by a center section or bight 13. The inner portion of the U consists of a plastic coating 15 which extends up both arms of the U for about one-third the height of the arms. The device 7 is cut across the grain so that one can see the end of the grain as at 17 and 19.

In FIG. 1, a pot 21 is shown which is largely filled with soil 23 with a plan 25 growing therein. The indicator 7 is partially buried in the soil as shown. If the soil is moist, the arms 9 and 11 will be pulled toward each other until they touch as is shown in solid lines. On the other hand, when the soil gets dry, the arms spread apart as is shown in dot-dash lines.

Figures 3, 4:
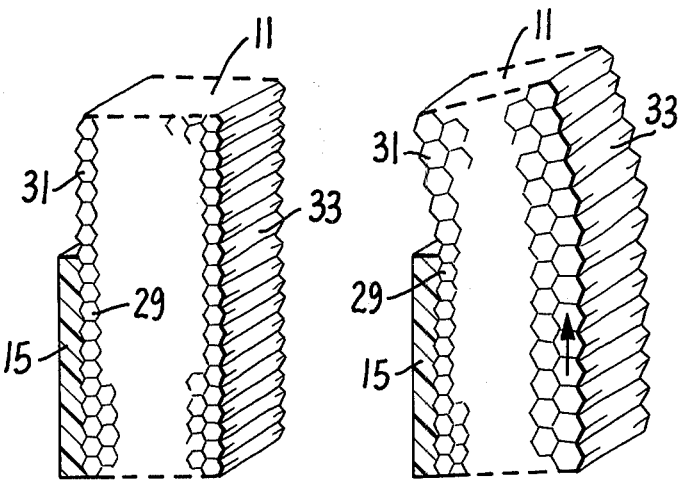
FIG. 3 is a section on the line 3—3 of FIG. 2.
FIG. 4 is a view similar to FIG. 3 showing the action when the indicator is moist.

The theory of operation is shown in FIGS. 3 and 4. Here one arm, 11, of the U-shaped structure is shown with the plastic member 15. Those cells which lie directly in contact with this plastic have been designated 29, while those above the plastic have been designated 31. The cells at the opposite side of the device have been designated 33. In FIG. 3, the device is shown when the wood is dry, and all of the cells, 29, 31 and 33, are substantially the same size. Now if one adds moisture to the structure, as is shown in FIG. 4, plastic 15 restrains the cells 29 and both protects them from getting wet and also serves to prevent them from expanding if they do get wet. On the other hand, the cells 31 and the cells 33 become wet and expand so that the column tilts to the left as is shown in FIG. 4, somewhat in the manner of a bimetallic strip.

Figure 5:
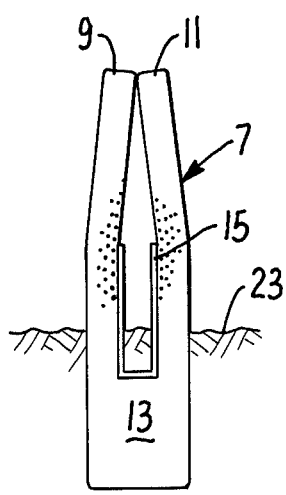
FIG. 5 shows the installation of the device in soil to measure the moisture near the surface of the soil.
Figure 6:
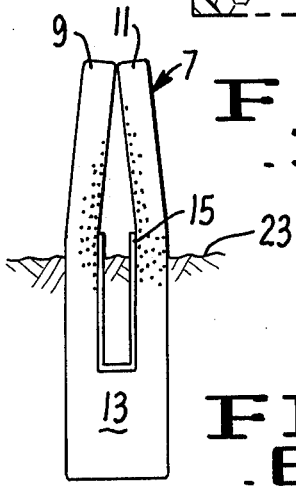
FIG. 6 shows the use of the device to measure moisture at a greater depth.

In FIGS. 5 and 6, it is shown how the device can be inserted in the soil at different depths depending on the moisture needs of a plant. In FIG. 5, the indicator 7 is inserted into the soil 23 so that the bottom portion 13 of the U is barely covered. This position is useful to indicate surface moisture. In FIG. 6, the device 7 is shown inserted into the soil almost to the top of the plastic insert 15. This position is useful for showing the moisture at substantial depth under the surface. Thus, it is easy to adjust the device of the present invention to indicate moisture depending upon the needs of the particular plant.

The plastic 15 must be of a rigid, waterproof adhesive, such as those epoxy cements which do not creep. If the cement is not waterproof, the cells can obviously expand adjacent to the plastic while if the plastic creeps, the differential effect which causes the leaning is largely lost. If the plastic creeps or flows, it will change the calibration of the device. The plastic must adhere to the wood.

Various woods may be used but it is preferred that the device be made of redwood because of its expansion characteristics and rsistance to decay. Cedar is also useful.

Although a preferred embodiment has been described, it will be obvious that many variations can be made on the exact structure shown without departing from the spirit of this invention.

I claim:

1. A soil moisture indicator comprising an elongated U-shaped member having a base adapted to be partially inserted for a portion of its length in soil with a bight of the U down and with the two arms of the U extending upwardly, said U being fabricated of wood and having a rigid, waterproof adhesive coating the bight and the lower portions of the inner surfaces of the arms of the U, the grain of the wood running at right angles to the longer dimension of the arms of the U, and the grain running parallel with the inner surfaces of the arms of the U-shaped member, the arms of said U above said coated portions being drawn towards each other in the presence of moisture and being spread apart when dry.

2. The indicator of claim 1 wherein the wood is redwood.

* * * * *